United States Patent [19]

Jeschke et al.

[11] Patent Number: 5,656,464
[45] Date of Patent: Aug. 12, 1997

[54] LACTIC-ACID-CONTAINING CYCLIC DEPSIPEPTIDES HAVING 18 RING ATOMS AS ENDOPARASITICIDAL AGENTS, AND PROCESS FOR THEIR PREPARATION

[75] Inventors: Peter Jeschke, Leverkusen; Achim Harder, Cologne; Norbert Mencke, Leverkusen; Horst Kleinkauf; Rainer Zocher, both of Berlin, all of Germany

[73] Assignee: Bayer Aktiengesellschaft, Leverkusen, Germany

[21] Appl. No.: 390,326

[22] Filed: Feb. 17, 1995

[30] Foreign Application Priority Data

Feb. 24, 1994 [DE] Germany .............. 44 06 025.4

[51] Int. Cl.$^6$ .............. C12P 17/00; C12P 17/14
[52] U.S. Cl. .............. 435/117; 435/68.1; 435/71.1; 435/120; 435/128; 435/132; 435/135; 435/136; 435/139; 435/147; 435/171; 530/317
[58] Field of Search .............. 435/117, 118, 435/119, 120, 128, 132, 136, 71.1, 68.1; 530/317

[56] References Cited

U.S. PATENT DOCUMENTS 3,937,718  2/1976  Mukaiyama .............. 548/475

FOREIGN PATENT DOCUMENTS 2851629  6/1979  Germany .
9325543  12/1993  WIPO .

OTHER PUBLICATIONS

M. Kobayashi et al., Anna Rep. Sankyo Res. Lab, vol. 46, 67–75 (1994).

Chemical Abstracts, abstract of 114: 227487k Abstract of JP 02-229,177 (1991).

H. Tomoda et al., J. Antibiotics, vol. 45, No. 8, pp. 1207–1215 (1992).

R. Pieper et al. J. Antibiotics, vol. 45, No. 8 pp. 1273–1277 (1992).

Primary Examiner—Blaine Lankford
Attorney, Agent, or Firm—Sprung Horn Kramer & Woods

[57] ABSTRACT

The present invention relates to a process for the preparation of lactic-acid-containing, optically active, cyclic depsipeptides having 18 ring atoms with the aid of fungal strains of the species Fusarium or enzymatic preparations isolated therefrom.

3 Claims, No Drawings

LACTIC-ACID-CONTAINING CYCLIC DEPSIPEPTIDES HAVING 18 RING ATOMS AS ENDOPARASITICIDAL AGENTS, AND PROCESS FOR THEIR PREPARATION

The present invention relates to a new process for the preparation of lactic-acid-containing cyclic depsipeptides having 18 ring atoms, some of these depsipeptides being known.

Certain lactic-acid-containing cyclic depsipeptides having 18 ring atoms (enniatins) and their use as endoparasiticides are already the subject of an earlier patent application (DE-OS (German Published Specification) 4 317 458).

A series of chemical and microbial processes exist for the preparation of cyclic depsipeptides which have 18 ring atoms and contain D-2-hydroxy-isovaleric acid. (for example by synthesis, cf.: P. Quitt et al., Helv. Chimica Acta 46 (1963) pp. 1715–1720; P. Quitt et al., Helv. Chimica Acta 47 (1964) pp. 166–173 [enniatin A]; Pl. A. Plattner et al., Helv. Chimica Acta 46 (1963) pp. 927–935 [enniatin B]; Yu. A. Ovchinnikov et al., Tetrahedron Lett. 2 (1971) pp. 159–162; R. W. Roeske et al., Biochem. Biophys. Res. Commun. 57 (1974) pp. 554–561 [beauvericin]; for example by fermentation, c.f.: R. Zocher et al., J. Antibiotics 45 (1992) pp. 1273–1277 [enniatins A, B and C]; A. Visconti et al., J. Agric. Food Chem. 40 (1992) pp. 1076–1082 [enniatin $B_4$]; Hiroshi Tomoda et al., J. Antibiotics 45 (1992) pp. 1207–1215 [enniatins A, $A_1$, B, $B_1$, D, E and F]).

The fermentation of a cyclohexadepsipeptide which contains D-2-hydroxy-sec-caproic acid is described in a Japanese patent (cf. synthesis of ME 1688: JP Patent 02 229 177 A2; Ref. C.A. 114 (23): 227 487k).

However, nothing has been disclosed about synthesizing lactic-acid-containing cyclohexadepsipeptides (enniatins) by means of fermentation.

The present invention relates to a process for the preparation of lactic-acid-containing, optically active, cyclic depsipeptides having 18 ring atoms with the aid of fungal strains of the species Fusarium, or enzymatic preparations isolated therefrom.

In the process according to the invention, the lactic-acid-containing, optically active, cyclic depsipeptides having 18 ring atoms (enniatins) of the general formula

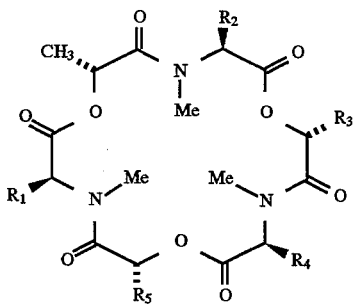

(I)

in which $R^1$, $R^2$ and $R^4$ independently of one another represent hydrogen, straight-chain or branched alkyl having up to 8 carbon atoms, hydroxyalkyl, mercaptoalkyl, alkylthioalkyl, alkylsulphinylalkyl, alkylsulphonylalkyl, carboxyalkyl, alkoxycarbonylalkyl, carbamoylalkyl, aminoalkyl, alkylaminoalkyl, dialkylaminoalkyl, guanidinoalkyl, straight-chain or branched alkenyl having up to 6 carbon atoms, cyclic alkyl having up to 8 carbon atoms, and optionally substituted arylalkyl or hetarylalkyl, substituents which may be mentioned being halogen, hydroxyl, alkoxy, alkyl, nitro or amino, $R^3$ and $R^5$ independently of one another represent hydrogen, straight-chain or branched alkyl having up to 8 carbon atoms, hydroxyalkyl, mercaptoalkyl, alkylthioalkyl, alkylsulphinylalkyl, alkylsulphonylalkyl, straight-chain or branched alkenyl having up to 6 carbon atoms, cyclic alkyl having up to 8 carbon atoms, and optionally substituted arylalkyl or hetarylalkyl, substituents which may be mentioned being halogen, hydroxyl, alkoxy, alkyl, nitro or amino, are prepared by reacting optically active racemic amino acids of the formulae (II), (III) and (IV)

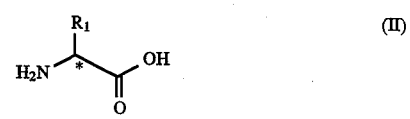

(II)

(III)

(IV)

in which $R^1$, $R^2$ and $R^4$ have the abovementioned meaning, with optically active or racemic 2-hydroxy-carboxylic acids of the formulae (V) and (VI)

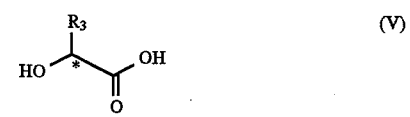

(V)

(VI)

in which $R^3$ and $R^5$ have the abovementioned meaning, and optically active or racemic lactic acid in the presence of fungal strains of the species Fusarium in suitable nutrient solutions or in a buffer system in the presence of synthetases isolated from microorganisms, and subsequently isolating the desired lactic-acid-containing cyclic depsipeptides having 18 ring atoms (enniatins).

The lactic-acid-containing cyclic depsipeptides having 18 ring atoms (enniatins) of the general formula (I) are outstandingly suitable for combating endoparasites, in particular in the field of medicine and veterinary medicine The general formula (I) provides a general definition of the lactic-acid-containing cyclic depsipeptides having 18 ring atoms (enniatins) according to the invention.

Preferred compounds of the general formula (I) are those in which $R^1$, $R^2$ and $R^4$ independently of one another represent hydrogen, straight-chain or branched $C_1$–$C_8$-alkyl, in particular methyl, ethyl, propyl, isopropyl, butyl, isobutyl, sec-butyl, tert-butyl, pentyl, sec-pentyl, 1,2-dimethylpropyl, neo-pentyl, 1-ethyl-propyl, 1,1,-dimethyl-propyl, hexyl, isohexyl, sec-hexyl, heptyl, isoheptyl, sec-heptyl, tert-heptyl, octyl, isooctyl, sec-octyl, hydroxy-$C_1$–$C_4$-alkyl, in particular hydroxymethyl, 1- and 2-hydroxyoxyethyl, mercapto-$C_1$–$C_4$-alkyl, in particular mercaptomethyl, $C_1$–$C_4$-alkylthio-$C_1$–$C_4$-alkyl, in particular methylthiomethyl, methylthioethyl, $C_1$–$C_4$-alkylsulphinyl-$C_1$–$C_4$alkyl, in particular methylsulphinylmethyl, methylsulphinyl ethyl, $C_1$–$C_4$-alkylsulphonyl-$C_1$–$C_4$-alkyl, in particular methylsulphonylmethyl, methylsulphonylethyl, carboxy-$C_1$–$C_6$-alkyl, in particular methoxycarbonylmethyl, ethoxycarbonylethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, guanido-$C_1$–$C_6$-alkyl, in particular guanidopropyl, $C_2$–$C_6$-alkenyl, in particular vinyl, allyl, butenyl, hexenyl, $C_3$–$C_7$-cyclo-$C_1$–$C_4$-alkyl, in particular cyclopropylmethyl, cyclopentylmethyl, cyclohexylmethyl, cycloheptylmethyl, hetaryl-$C_1$–$C_4$-alkyl, in particular thien-2-yl-methyl, thien-3-yl-methyl, indol-3-yl-methyl, phenyl-$C_1$–$C_4$-alkyl, in particular phenylmethyl which can optionally be substituted by radicals from the series comprising halogen, in particular fluorine, chlorine, bromine or iodine, hydroxyl, nitro, amino, $C_1$–$C_4$-alkoxy, in particular methoxy or ethoxy and $C_1$–$C_4$-alkyl, in particular methyl, $R^3$ and $R^5$ independently of one another represent hydrogen, straight-chain or branched $C_1$–$C_8$-alkyl, in particular methyl, ethyl, propyl, isopropyl, butyl, isobutyl, sec-butyl, tert-butyl, pentyl, sec-pentyl, 1,2-dimethylpropyl, neo-pentyl, 1-ethyl-propyl, 1,1-dimethyl-propyl, hexyl, isohexyl, sec-hexyl, heptyl, isoheptyl, sec-heptyl, tert-heptyl, octyl, isooctyl, sec-octyl, hydroxy-$C_1$–$C_4$-alkyl, in particular hydroxymethyl, 1-and 2-hydroxyoxyethyl, mercapto-$C_1$–$C_4$-alkyl, in particular mercaptomethyl, $C_1$–$C_4$-alkylthio-$C_1$–$C_4$-alkyl, in particular methylthiomethyl, methylthioethyl, $C_1$–$C_4$-alkylsulphinyl-$C_1$–$C_4$-alkyl, in particular methylsulphinylmethyl, methylsulphinylethyl, $C_1$–$C_4$-alkylsulphonyl-$C_1$–$C_4$-alkyl, in particular methylsulphonylmethyl, methylsulphonylethyl, $C_2$–$C_6$-alkenyl, in particular vinyl, allyl, butenyl, hexenyl, $C_3$–$C_7$-cyclo-$C_1$–$C_4$-alkyl, in particular cyclopropylmethyl, cyclopentylmethyl, cyclohexylmethyl, cycloheptylmethyl, hetaryl-$C_1$–$C_4$-alkyl, in particular thien-2-yl-methyl, thien-3-yl-methyl, phenyl-$C_1$–$C_4$-alkyl, in particular phenylmethyl which can optionally be substituted by radicals from the series comprising halogen, in particular fluorine, chlorine, bromine or iodine, hydroxyl, nitro, amino, $C_1$–$C_4$-alkoxy, in particular methoxy or ethoxy, and $C_1$–$C_4$-alkyl, in particular methyl.

Particularly preferred compounds of the general formula (I) are those in which $R^1$, $R^2$ and $R^4$ independently of one another represent straight-chain or branched $C_1$–$C_8$-alkyl, in particular methyl, ethyl, propyl, isopropyl, butyl, isobutyl, sec-butyl, pentyl, sec-pentyl, 1,2-dimethyl-propyl, neo-pentyl, 1-ethyl-propyl, 1,1-dimethyl-propyl, hexyl, isohexyl, sec-hexyl, heptyl, isoheptyl, sec-heptyl, octyl, isooctyl, sec-octyl, hydroxy-$C_1$–$C_4$-alkyl, in particular hydroxymethyl, 1- and 2- hydroxyoxyethyl, mercapto-$C_1$–$C_4$-alkyl, in particular mercaptomethyl, $C_1$–$C_4$-alkylthio-$C_1$–$C_4$-alkyl, in particular mercaptomethyl, methylthioethyl, $C_2$–$C_6$-alkenyl, in particular vinyl, ally, butenyl, hexenyl, $C_3$–$C_7$ -cyclo-$C_1$–$C_4$-alkyl, in particular cyclopropylmethyl, cyclopentylmethyl, cyclohexylmethyl or cycloheptylmethyl, $R^3$ and $R^5$ independently of one another represent straight-chain or branched $C_1$–$C_8$-alkyl, in particular methyl, ethyl, propyl, isopropyl, butyl, isobutyl, sec-butyl, tert-butyl, pentyl, sec-pentyl, 1,2-dimethylpropyl, neo-pentyl, 1-ethyl-propyl, 1,1-dimethylpropyl, hexyl, isohexyl, sec-hexyl, heptyl, isoheptyl, sec-heptyl, tert-heptyl, octyl, isooctyl, sec-octyl, hydroxy-$C_1$–$C_4$-alkyl, in particular hydroxymethyl, 1- and 2 -hydroxyoxyethyl, $C_1$–$C_4$-alkylthio-$C_1$–$C_4$-alkyl, in particular methylthiomethyl, $C_2$–$C_6$-alkenyl, in particular vinyl, allyl, butenyl, hexenyl, $C_3$–$C_7$-cyclo-$C_1$–$C_4$-alkyl, in particular cyclopropylmethyl, cyclopentylmethyl, cyclohexylmethyl or cycloheptylmethyl.

Very particularly preferred compounds of the formula (I) are those in which $R^1$, $R^2$ and $R^4$ independently of one another represent straight-chain or branched $C_1$–$C_6$-alkyl, in particular methyl, ethyl, propyl, isopropyl, butyl, isobutyl, sec-butyl, pentyl, sec-pentyl, 1,2-dimethyl-propyl, neo-pentyl, 1-ethylpropyl, 1,1-dimethyl-propyl, hexyl, isohexyl, sec-hexyl, heptyl, isoheptyl, sec-heptyl, octyl, isooctyl, sec-octyl, $C_2$–$C_6$-alkenyl, in particular vinyl, allyl, butenyl, $C_3$–$C_7$-cyclo-$C_1$–$C_4$-alkyl, in particular cyclohexylmethyl, $R^3$ and $R^5$ independently of one another represent straight-chain or branched $C_1$–$C_8$-alkyl, in particular methyl, ethyl, propyl, isopropyl, butyl, isobutyl, sec-butyl, tert-butyl, pentyl, sec-pentyl, 1,2-dimethyl-propyl, neo-pentyl, 1-ethyl-propyl, 1,1-dimethyl-propyl, hexyl, isohexyl, sec-hexyl, heptyl, isoheptyl, sec-heptyl, tert-heptyl, octyl, isooctyl, sec-octyl, $C_2$–$C_6$-alkenyl, in particular vinyl, allyl, butenyl, hexenyl, $C_3$–$C_7$-cyclo-$C_1$–$C_4$-alkyl, in particular cyclohexylmethyl.

The following optically active compounds of the general formula (I) may be mentioned individually:

cyclo(-N-methyl-L-alanyl-D-lactyl-N-methyl-L-isoleucyl-D-lactyl-N-methyl-L-valyl-D-lactyl-), cyclo(-N-methyl-L-alanyl-D-lactyl-N-methyl-L-isoleucyl-D-lactyl-N-methyl-L-norvalyl-D-lactyl-), cyclo(-N-methyl-L-alanyl-D-lactyl-N-methyl-L-isoleucyl-D-lactyl-N-methyl-L-leucyl-D-lactyl-), cyclo(-N-methyl-L-alanyl-D-lactyl-N-methyl-L-isoleucyl-D-lactyl-N-methyl-L-norleucyl-D-lactyl-), cyclo(-N-methyl-L-valyl-D-lactyl-N-methyl-L-valyl-D-2-hydroxy-isovaleryl-N-methyl-L-valyl-D-lactyl-), cyclo(-N-methyl-L-valyl-D-2-hydroxy-isovaleryl-N-methyl-L-valyl-D-2-hydroxy-isovaleryl-N-methyl-L-valyl-D-lactyl-), cyclo(-N-methyl-L-alanyl-D-lactyl-N-methyl-L-alloisoleucyl-D-lactyl-N-methyl-L-alloisoleucyl-D-lactyl-), cyclo(-N-methyl-L-alanyl-D-lactyl-N-methyl-L-alloisoleucyl-D-lactyl-N-methyl-L-alanyl-D-lactyl-), cyclo(-N-methyl-L-alanyl-D-lactyl-N-methyl-L-isoleucyl-D-lactyl-N-methyl-L-2-amino-butyryl-D-lactyl-), cyclo(-N-methyl-L-alanyl-D-lactyl-N-methyl-L-alloisoleucyl-D-lactyl-N-methyl-L-2-amino-butyryl-D-lactyl-).

Some of the compounds of the general formula (I) are known (cf., for example V. Z. Pletnev et al. Bioorg. Khim.

1 (2) (1975) pp. 160–165; ref. C.A. 83 (13): 114 872e; DE-OS (German Published Specification) 4 317 458 and can also be obtained by the chemico-synthetic processes described therein.

If, in the process according to the invention for the preparation of the lactic-acid-containing cyclic depsipeptides (enniatins) (I), L-valine ($R^1$, $R^2$ and $R^4$: -isopropyl) is used as compounds of the formulae (II) to (IV) and D-lactic acid ($R^3$ and $R^5$: -methyl) as compounds of the formulae (V) and (VI), the process can be described, for example, by the following equation:

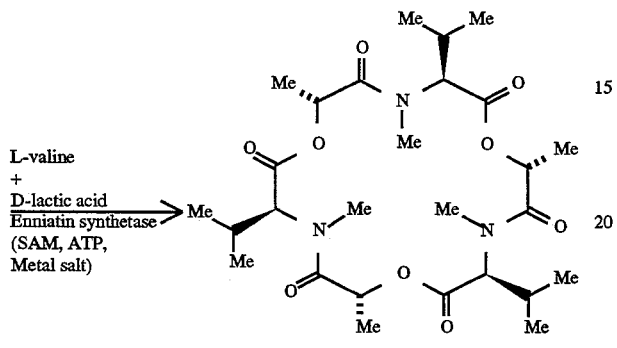

SAM: S-adenosyl-L-methionine
ATP: Adenosine triphosphate
Metal salt: For example alkaline earth metal salt ($Mg^{2+}$ salt) or $Mn^{2+}$ salt.

Formulae (II) to (IV) provide general definitions of the amino acids required as starting compounds for carrying out the process according to the invention. In these formulae, $R^1$, $R^2$ and $R^4$ preferably represent those radicals which have already been mentioned in connection with the description of the substances of the formula (I) according to the invention as being preferred for these substituents.

If the natural or synthetic amino acids which are used as starting substances are chiral, they can exist in the D or L form. However, alpha-amino acids in the L configuration are preferred.

Examples which may be mentioned are: Aad, Abu, jAbu, ABz, 2ABz, εAca, Ach, Acp, Adpd, Ahb, Aib, βAib, Ala, βAla, ΔAla, Alg, All, Ama, Amt, Ape, Apm, Apr, Arg, Ash, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guy, hAla, hArg, hCys, hGln, hGlu, His, hIle, hLeu, hLys, hMet, hPhe, hPro, hSer, hThr, hTrp, hTyr, HyI, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sat, Sec, Sem, Set, Thi, βThi, Thr, Thy, Thx, Tia, Tle, Tly, Trp, Trta, Tyr, Val, Nal, Tbg, Npg, Chg, Thia, (cf., for example, Houben-Weyl, Methoden der Organischen Chemie [Methods in Organic Chemistry], Volumes XV/1 and 2, Stuttgart, 1974).

Formulae (V) to (VI) provide general definitions of the 2-hydroxy-carboxylic acids required as starting substances for carrying out the process according to the invention.

In these formulae: $R^3$ and $R^5$ preferably represent those radicals which have already been mentioned in connection with the description of the substances of the formula (I) according to the invention as being preferred for these substituents.

If the 2-hydroxy-carboxylic acids which are used as starting substances are chiral, they can exist in the D or L form. However, the 2-hydroxycarboxylic acids which have the D configuration are preferred.

Examples which may be mentioned are the following:

Hyac, Hyba, Hydd, Hyde, Hyic, Hyiv, Hymb, Hypp, Hypr (Lac), Hytd, Hyud, Hyva, (cf., for example, Houben-Weyl, Methoden der Organischen Chemie [Methods in Organic Chemistry], Volumes XV/1 and 2, Stuttgart, 1974).

Fusarium strains which are suitable for carrying out the process according to the invention are the Fusarium strains which follow.

| Fusarium strain | | isolated from |
|---|---|---|
| *Fusarium acuminatum* | | |
| 3RA 61 148 | | blue lupin |
| *Fusarium arthrosporoides* | | |
| BBA 64 134 | | bent grass (seeds) |
| *Fusarium avenaceum* | | |
| BBA 64 336 | | winter barley (seeds) |
| BBA 62 163 | | cabbage |
| *Fusarium compactum* | | |
| BBA 65 671 | | cotton |
| *Fusarium crookwellense* | | |
| BBA 64 297 | | wheat (stem base) |
| *Fusarium ensiforme* | | |
| BBA 64 683 | | sweet potato |
| *Fusarium equiseti* | | |
| BBA 64 814 | | rye |
| *Fusarium inflexum* | | |
| BBA 63 203 | | field bean |
| *Fusarium gibbosum* | | |
| *Fusarium lateritium* | | |
| BBA 65 090 | | wheat (stem base) |
| *Fusarium meresmoides* | | |
| BBA 64 329 | | rye (stem base) |
| *Fusarium moniliforme* | | |
| *Fusarium oxysporum* | | |
| BBA 62 057 | f. pisi | pea |
| BBA 62 060 | f. lycopersici | tomato |
| BBA 62 334 | f. lupini | white lupin |
| BBA 64 952 | f. batatas | sweet potato |
| *Fusarium proliferatum* | | |
| BBA 63 625 | | dragon tree |
| *Fusarium redolens* | | |
| BBA 62 390 | | gillyflower |
| *Fusarium sambucinum* | | |
| BBA 63 933 | | wheat |
| BBA 62 397 | | potato |
| NRRL-13 500 | | potato |
| NRRL-13 503 | | potato |
| R-383 | | poligonum |
| R-5390 | | potato |
| R-7370 | | soil |
| R-5455 | | cereals |
| A-6380 | | potato |
| R-7843 | | pink |
| R-5690 | | soil |
| R-2633 | | potato |
| R-6354 | | cereals |
| *Fusarium scirpi* | | |
| ETH 64 1536 | | grassland soil |

| Fusarium strain | | isolated from |
| --- | --- | --- |
| *Fusarium semitectum* | | |
| *Fusarium solani* | | |
| BBA 64 953 | | sweet potato |
| BBA 62 420 | f. pisi | pea |
| *Fusarium subglutinans* | | |
| *Fusarium tricinctum* | | |
| BBA 62 446 | | red clover |
| *Fusarium udum* | | |
| BBA 62 451 | | Cajanus inidians |

Particular mention must be made of the Mintolyte Fusarium strains DSM 8938 and DSM 8939, which were deposited on 31 Jan. 1994 at the Deutsche Sammlung für Mikroorganismen (DSM); (German Collection of Microorganisms) in Brunswick in accordance with the Budapest Treaty.

The process can also be carried out using synthetases isolated from microorganisms. The enniatin synthetases required for this purpose can be isolated from the Fusarium strains mentioned further above using processes known from the literature (cf. for example: R. Pieper, H. Kleinkauf, R. Zocher, J. Antiblot. 45(1993) pp. 1273–1277).

The fungal strains of the species Fusarium are fermented by methods known per se in the presence of suitable nutrient solutions. These nutrient solutions contain the salts which are required for the fungal growth, as well as carbon and nitrogen sources.

Suitable inorganic salts for carrying out the process according to the invention are all alkali metal salts, alkaline earth metal salts and metal salts with elements of sub-groups II to VIII of the Periodic Table.

Examples which may be mentioned are the acetates, chlorides, bromides, iodides, fluorides, nitrates, nitrites, phosphates, hydrogenphosphates, dihydrogenphosphates, phosphites, hydrogenphosphites, sulphates, hydrogensulphates, sulphites, hydrogensulphites, carbonates or hydrogencarbonates of lithium, sodium, potassium, caesium, magnesium, calcium, barium, zinc, cadmium, scandium, titanium, zirconium, vanadium, niobium, chromium, molybdenum, manganese, iron, cobalt or nickel.

Substances which are preferably used are acetates, halides, phoshates, hydrogenphosphates, dihydrogenphosphates, nitrates of the alkali metals, in particular sodium and potassium, the sulphates of the alkaline earth metals, in particular magnesium, and metals of sub-groups II, VII and VIII of the Periodic Table, for example zinc, manganese and iron.

Carbon sources for carrying out the process according to the invention are carbohydrates and carbohydrate-containing products.

Examples which may be mentioned are the monosaccharides, such as pentoses, in particular ribose, the hexoses, in particular glucose and fructose, the oligosaccharides, such as disaccharides, in particular sucrose, maltose and lactose, the trisaccharides, in particular raffinose, as well as tetra-, penta- and hexasaccharides.

Monosaccharides, such as, for example, hexoses, in particular glucose, oligosaccharides, such as, for example, disaccharides, in particular sucrose are preferably used.

Suitable nitrogen sources for carrying out the process according to the invention are amino acids and nitrogen-containing salts.

Examples which may be mentioned are the natural and synthetic amino acids which have been mentioned further above, or nitrogen-containing salts, such as ammonium nitrate, ammonium nitrite, or the nitrates and nitrites of the metals which have been mentioned further above.

The natural amino acids which have been mentioned further above, and nitrogen-containing salts, such as ammonium nitrate are preferably used.

The Fusarium strains used for the fermentative process are first grown by methods known per se in a medium which is composed of, for example, molasses/cornsteep liquor. After they have been grown, the spores formed are isolated by means of spore filters. To produce the preculture, a Fusarium defined medium (FDM), composed of a carbon source and inorganic salts, is inoculated with approximately $10^9$ spores and refermented. After a few days, the FDM main culture can be prepared by inoculation with 1 ml of preculture, and fermentation can be carried out analogously.

The actual fermentation is then carried out in the presence of compounds of the formulae (II) to (IV) or (V) and (VI) and in the presence of optically active or racemic lactic acid.

The fermentation time is 1 to 30 days. The fermentation is carried out at temperatures between +5° C. and +40° C., preferably between +15° C. and +35° C., particularly preferably between +25° C. and +30° C. The process is carried out under sterile conditions and under atmospheric pressure.

To carry out the process, the compounds of the formulae (V) and (VI) are generally employed at a concentration of 5 mM to 50 mM, preferably 5 mM to 15 mM.

After the fermentation has ended, the mycelium of the Fusarium culture is filtered off with suction, homogenized extracted repeatedly with an organic solvent, and then filtered. The culture filtrate obtained is extracted in the customary manner, dried and concentrated in vacuo.

The crude enniatins obtained can be purified in the customary manner by column chromatography or counter-current distribution. The optimum procedure must be determined in each individual case (cf. also the Preparation Examples).

If the process according to the invention is carried out in the presence of isolated synthetases, it is carried out using an aqueous buffer system in the presence of metal salts, S-adenosyl-L-methionine (SAM) and adenosine triphosphate (ATP). Metal salts which may be mentioned are: acetates, chlorides, bromides, iodides, fluorides, nitrates, phosphates, hydrogenphosphates, phosphites, hydrogenphosphites, sulphates, hydrogensulphates, sulphites, hydrogensulphites, carbonates and hydrogencarbonates of lithium, sodium, potassium, caesium, magnesium, calcium or barium.

Salts which are preferably used are alkaline earth metal salts, such as, for example, magnesium chloride, magnesium sulphate or magnesium acetate.

The process according to the invention is carried out in an aqueous buffer solution.

Examples which may be mentioned are commercially available buffer solutions, for example for a pH of 1.0, in particular glycine/hydrochloric acid, for a pH of 2.0 to 4.0, in particular citrate/hydrochloric acid, for a pH of 5.0 to 6.0, in particular citrate/sodium hydroxide solution, for a pH of 7.0, in particular phosphate, for a pH of 8.0, in particular borate/hydrochloric acid, and for a pH of 9.0 to 10.0, in particular boric acid/potassium chloride/sodium hydroxide solution.

It is preferred to operate within the "physiological range", i.e. at a pH of 6.0 to 9.0, for which it is preferred to use a phosphate buffer solution, in particular potassium hydrogenphosphate/disodium hydrogenphosphate or potassium hydrogenphosphate/dipotassium hydrogenphosphate.

To carry out the process, 2 mM to 8 mM, preferably 3 mM to 5 mM of compounds of the formulae (II) to (VI), optically active or racemic lactic acid and S-adenosyl-L-methionine (SAM), 3 mM to 9 mM, preferably 4 mM to 6 mM, of adenosine triphosphate (ATP), 2 mM to 25 mM, preferably 5 mM to 15 mM, of alkaline earth metal salt, 10 mM to 100 mM, preferably 40 mM to 60 mM of buffer, are generally employed together with 100 μg to 1000 μ, preferably 200 μg to 600 μg, of isolated enniatin synthetase in vitro.

The reaction time of the enzymatic in-vitro synthesis is 2 minutes to 24 hours. The enzymatic in-vitro synthesis is carried out in a temperature range 0° C. to +50° C., preferably at +10° C. to +35° C., particularly preferably between +20° C. and +30° C.

It proceeds in a pH range of 6.5 to 8.5, preferably at 7.0 to 8.0, the pH being kept at a constant 7.3 during the entire reaction by adding a buffer.

The process is preferably carried out under sterile reaction conditions and under atmospheric pressure.

The enzymatic in-vitro synthesis can be stopped by diluting with water.

For working up, the aqueous phase is extracted repeatedly with an organic solvent, and the extract is dried and concentrated in vacuo.

The crude enniatins obtained can be purified in the customary manner by column chromatography or by counter-current distribution. Again, the ideal procedure will have to be determined in each individual case (cf. also the Preparation Examples).

PREPARATION EXAMPLES

Example 1

Preparation of cyclo (-N-methyl-L-valyl-D-lactyl-N-methyl-L-valyl-D-lactyl-N-methyl-L-valyl-D-lactyl-)

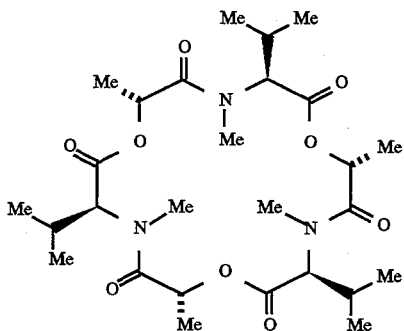

In-vivo incorporation of D-lactic acid

D-lactic acid is added under sterile conditions to a 2-day-old main culture of *Fusarium scirpi*, at a concentration of 10 mM, and the fermentation is continued for another 3 days. The mycelium of the Fusarium culture is then filtered off with suction, and the filtrate is extracted three times using ethyl acetate. The mycelium is homogenized twice in a mortar using acetone, and the homogenate is subsequently subjected to filtration with suction. The culture filtrate is extracted by shaking three times with in each case 100 ml of ethyl acetate, and the combined organic phases, together with the acetone extract are evaporated to dryness.

Alternatively, the entire Fusarium culture can be extracted overnight in approximately twice its volume of ethyl acetate.

To concentrate the enniatin by column chromatography, the crude enniatin, which is dissolved in a small amount of chloroform, is applied to an $Al_2O_3$ column (30×2 cm) and eluted stepwise.

Enzymatic in-vitro synthesis

300–500 μg of purified enniatin synthetase in 50 mM of phosphate buffer (pH 7.3) are incubated for 10 minutes at 28° C. in a total volume of 1.5 ml in the presence of 4 mM L-valine, 4 mM D-lactic acid, 4 mM S-adenosyl-L-methionine (SAM), 5 mM adenosine triphosphate (ATP) and 10 mM $MgCl_2$.

After adding of 2 ml of water.

the mixture is extracted repeatedly using 2 ml portions of ethyl acetate. The organic phase is dried using sodium sulphate and then concentrated in vacuo.

The product which has been obtained by a) or b) is purified by means of preparative HPLC (RP 18/75–80% methanol).

$^1$H NMR (400 MHz, $CDCl_3$, δ): 0.83; 1.03 (d, 18H, 3×—CH(C$\underline{H}_3$)$_2$); 1.45 (d, 9H, 3×—O—C$\underline{H}_3$); 2.27 (m, 3H, 3×—C$\underline{H}$(CH$_3$)$_2$); 3.06 (s, 9H, 3×—N—C$\underline{H}_3$); 4.43 (d, 3H, 3×—N—C$\underline{H}$—CO—); 5.62 (q, 3H, 3×—O—C$\underline{H}$—CO—) ppm $^{13}$C NMR (100 MHz, $CDCl_3$, δ): 16.5 (3×—$\underline{C}H_3$, D-Lac); 18.5; 20.1 (6×—$\underline{C}H_3$, MeVal); 27.8 (3×—$\underline{C}H(CH_3)_2$, L-MeVal); 32.9 (3×—N—$\underline{C}H_3$, L-MeVal); 63.1 (3×—N—$\underline{C}H$—CO—, L-MeVal); 66.3 (3×—O—$\underline{C}H$—CO—, D-Lac); 169.2 (3×—$\underline{C}$=O, amide); 169.8 (3×—$\underline{C}$=O, ester) ppm EI MS m/z (%): 555 (M$^+$, 32); 482 (20); 353 (1); 268 (34); 168 (100); 86 (53)

Example 2

Preparation of cyclo(-N-methyl-L-isoleucyl-D-lactyl-N-methyl-L-isoleucyl-D-lactyl-N-methyl-L-isoleucyl-D-2-hydroxy-isovaleryl-)

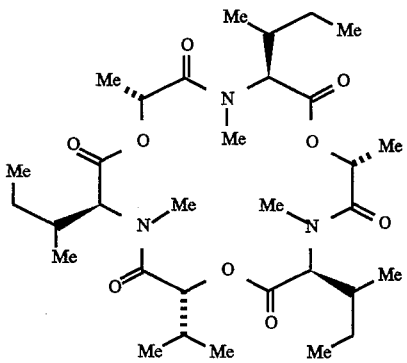

In-vivo incorporation of D-lactic acid

D-lactic acid is added under sterile conditions to a 2-day-old main culture of *Fusarium sambucinum*, at a concentration of 10 mM, and the fermentation is continued for another 3 days. The mycelium of the Fusarium culture is then filtered off with suction, and the filtrate is extracted three times using ethyl acetate. The mycelium is homogenized twice in a mortar using acetone, and the homogenate is subsequently subjected to filtration with suction. The culture filtrate is extracted by shaking three times with in each case 100 ml of ethyl acetate, and the combined organic phases, together with the acetone extract are evaporated to dryness. Concentration and purification of the enniatin are carried out as described in Example 1.

$^{13}$C NMR (100 MHz, $CDCl_3$, δ): 18.4; 18.0 (2×—$\underline{C}H_3$, D-HyIv); 16.8; 15.8 (2×—$\underline{C}H_3$, D-Lac); 16.7; 15.3; 11.4; 10.6; 10.3; 10.0 (6×—$\underline{C}H_3$, L-MeIle); 25.0; 24.9; 24.4

(3×—CH$_2$—, L-MeIle); 34.7; 34.1; 32.3 (3×—CH(CH$_3$)—, L-MeIle); 35.6; 31.6; 31.2 (3×—N—CH$_3$, L-MeIle); 29.9 (—CH(CH$_3$)$_2$, D-HyIv); 74.0; 67.5; 66.1 (3×—O—CH—CO—, D-HyIv); 65.1; 60.5; 59.5; (3×—N—CH—CO—, L-MeIle); 169.2; 169.1; 169.0 (3×—C=O, amide); 170.6; 170.1; 169.8 (3×—C=O, ester) ppm EI MS m/z (%): 625 (M$^+$, 23); 552 (14); 409 (5); 296 (20); 182 (43); 100 (100)

Analogously, the compounds of the general formula (I) listed in Table I below can be prepared in the form of LDLDLD stereoisomers.

g of MgSO$_4$·7 H$_2$O, 4.0 g of KH$_2$PO$_4$·7 H$_2$O, 10 g of ZnSO$_4$ per liter) is inoculated with 10$^9$ spores and fermented as above.

After 2 to 3 days, FDM main cultures are prepared by using in each case 1 ml of preculture as inoculum, and fermented as above.

Preparations for the in-vitro synthesis aimed at producing enniatin 2- to 3-day-old main cultures are first examined for their enniatin titers to ensure that the cells are actively synthetizing. To this end, 3 to 5 ml of culture are sampled under sterile

TABLE 1

Examples of compounds of the general formula (I)

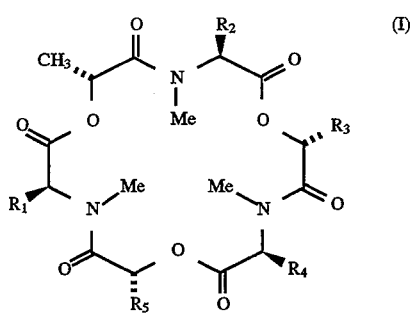

| Ex.-No. | Radical R$^1$ | Radical R$^2$ | Radical R$^3$ | Radical R$^4$ | Radical R$^5$ | Physical data[a] |
|---|---|---|---|---|---|---|
| 3 | -s-C$_4$H$_9$ | -s-C$_4$H$_9$ | —CH$_3$ | -s-C$_4$H$_9$ | —CH$_3$ | 33.9(—N—CH$_3$); 61.9 (—N—CH—); 66.4(—O—CH—); 169.3 (—CO—N—); 169.9(—CO—O—); 598(M$^+$+H, 12); 597(37); 541(42); 524 (14; 182(100) |
| 4 | -i-C$_4$H$_9$ | -i-C$_4$H$_9$ | —CH$_3$ | -i-C$_4$H$_9$ | —CH$_3$ | 32.0(—N—CH$_3$); 55.8 (—N—CH—); 67.0(—O—CH—); 169.4 (—CO—N—); 170.5(—CO—O—); 597(M$^+$, 22) ; 524(7) ; 381(1) 296(15); 182(100); 100(78) |
| 5 | —CH$_3$ | -s-C$_4$H$_9$ | —CH$_3$ | -s-C$_4$H$_9$ | —CH$_3$ | 32.8; 33.9; 34.2(—N—CH$_3$); 56.2; 59.9; 60.5(—N—CH—); 66.0; 66.3; 67.7(—O—CH—); 168.7; 169.7; 170.1(—CO—N—); 169.0; 170.0; 170.4(—CO—O—); 555(M$^+$, 64) ; 499(37) ; 428 (12); 357(19); 182(100); 100(52) |
| 6 | —CH$_3$ | -s-C$_4$H$_9$ | —CH$_3$ | —CH$_3$ | —CH$_3$ | 31.8; 33.8; 34.6(—N—CH$_3$); 168.1; 168.7; 169.9(—CO—N—); 170.0; 170.4; 170.5(—CO—O—); 513(M$^+$, 42); 440(22); 255 (29); 213(60); 182(75); 58(100) |
| 7 | -i-C$_3$H$_7$ | -i-C$_3$H$_7$ | -i-C$_3$H$_7$ | -i-C$_3$H$_7$ | -i-C$_3$H$_7$ | 611(M$^+$, 29); 528(15); 196 (100) |

[a] $^{13}$C NMR (100 MHz, CDCl$_3$, δ); FAB-MS or EI MS m/z (%)

Spore culture, precultures and main cultures

The Fusarium strain in question is grown in a medium composed of molasses/cornsteep liquor (30 g and 10 g/l, respectively).

The culture is grown in 500 ml Erlenmeyer flasks (100 ml of medium) at 100 rpm (26° to 28° C.). After 4 to 5 days, the spores which have formed are isolated by means of a spore filter. These spores can be kept for weeks at 4° C.

To prepare a preculture, a flask containing 200 ml of FDM (75.0 g of sucrose, 12.75 g of NaNO$_3$, 15.0 g of NaCl, 7.5 conditions and extracted repeatedly using in each case 2 ml of ethyl acetate. After evaporating the organic phase, the enniatin is examined directly by HPLC (RP 18.80% methanol).

The main cultures in question are treated under sterile conditions with the corresponding precursor hydroxy- or amino acid to an end concentration of 10 mM, and the fermentation is continued as described in Example 1 (total fermentation time approximately 1 week).

We claim:

1. A process for the preparation of lactic-acid-containing, optically active, cyclic depsipeptides having 18 ring atoms (enniatins) of the formula (I)

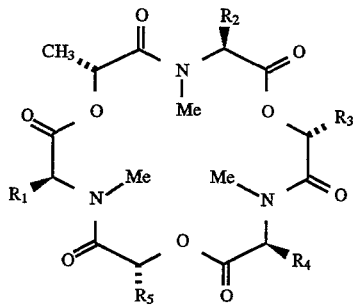 (I)

in which

R$^1$, R$^2$ and R$^4$ independently of one another represent straight-chain or branched alkyl having up to 8 carbon atoms, hydroxyalkyl, alkylthioalkyl, carboxyalkyl, carbamoylalkyl, aminoalkyl, straight-chain or branched alkenyl having up to 6 carbon atoms, or cyclic alkyl having up to 8 carbon atoms, and R$^3$ and R$^5$ independently of one another represent straight-chain alkyl, hydroxyalkyl, or alkylthioalkyl each having up to 6 carbon atoms, by reacting optically active or racemic amino acids of the formulae (II), (III) and (IV)

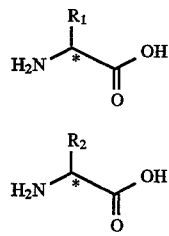 (II)

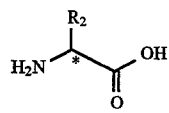 (III)

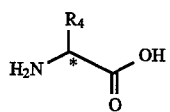 (IV)

and optically active or racemic 2-hydroxy-carboxylic acids of the formulae (V) and (VI)

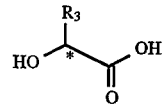 (V)

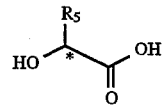 (VI)

and optically active or racemic lactic acid, the reaction being carried out in the presence of a fungal strain selected from the group consisting of Fusarium DSM 8938 or DSM 8939 in suitable nutrient solutions.

2. The process according to claim 1, in which

R$^1$, R$^2$ and R$^4$ independently of one another represent straight-chain or branched alkyl having up to 6 carbon atoms, or straight-chain or branched alkenyl having up to 6 carbon atoms, and R$^3$ and R$^5$ independently of one another represent straight-chain alkyl or hydroxyalkyl having up to 6 carbon atoms.

3. The process according to claim 1, in which

R$^1$, R$^2$ and R$^4$ independently of one another represent straight-chain or branched alkyl having up to 6 carbon atoms, or straight-chain or branched alkenyl having up to 6 carbon atoms, and R$^3$ and R$^5$ independently of one another represent straight-chain alkyl having up to 6 carbon atoms.

* * * * *